United States Patent [19]
Uldrikis et al.

[11] 4,293,700
[45] Oct. 6, 1981

[54] 2,6-DIMETHYL-1,4-DIHYDROPYRIDINE-3,5-DICARBOXYLIC ACID ESTERS AND METHOD FOR PREPARING SAME

[76] Inventors: Yan R. Uldrikis, ulitsa Darza, 2, kv. 2, Elgava; Ieva E. Preisa, ulitsa Lachplesha, 44/46, kv. 14, Riga; Gunar Y. Dubur, ulitsa Ierikju, 43, kv. 2, Riga; Aina A. Zidermane, ulitsa F. Engelsa, 11-a, kv. 9, Riga; Egils A. Biseniex, Talavas Gatve, 11, kv. 15, Riga; Gunar D. Tirzit, ulitsa Zhagatu, 22, kv. 33, Riga, all of U.S.S.R.

[21] Appl. No.: 137,012

[22] Filed: Apr. 3, 1980

[30] Foreign Application Priority Data

Aug. 8, 1978 [SU] U.S.S.R. .......................... 2655083[I]

[51] Int. Cl.³ .................. C07D 213/80; C07D 211/90
[52] U.S. Cl. ..................................... 546/321; 424/263
[58] Field of Search ............................... 546/321, 299

[56] References Cited

U.S. PATENT DOCUMENTS 4,214,088 7/1980 Abeler et al. ...................... 546/321
4,239,893 12/1980 Pigerol et al. ..................... 546/321

FOREIGN PATENT DOCUMENTS 2844130 10/1978 Fed. Rep. of Germany ...... 546/321

*Primary Examiner*—John D. Randolph
*Attorney, Agent, or Firm*—Steinberg & Raskin

[57] ABSTRACT

2,6-Dimethyl-1,4-dihydropyridine-3,5-dicarboxylic acid esters of the general formula:

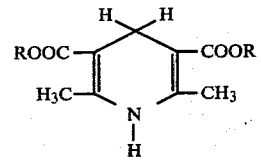

wherein R is a substituted alkyl or terpenyl.

A method for preparing said esters comprises reacting esters of acetoacetic acid of the general formula: $CH_3COCH_2COOR$, wherein R is a substituted alkyl or terpenyl, with hexamethylenetetramine in the presence of ammonium acetate in ethanol at its boiling temperature; said esters of acetoacetic acid of the above general formula, hexamethylenetetramine and ammonium acetate can be used in stoichiometric proportions.

2 Claims, No Drawings

2,6-DIMETHYL-1,4-DIHYDROPYRIDINE-3,5-DICARBOXYLIC ACID ESTERS AND METHOD FOR PREPARING SAME

FIELD OF THE INVENTION

The present invention relates to compounds possessing antimetastatic properties and low toxicity and to methods for preparing these compounds.

BACKGROUND OF THE INVENTION

The antimetastatic therapy is a new field of chemotherapy of tumors and is very promising, since it opens wide opportunites for surgical intervention, inhibiting or even eliminating the origination of metastases (secondary tumors) after the removal of the primary tumor. It is known (British Medical Journal, vol. 1, No. 5800, 1972, A. W. Le Serve, K. Hellmann "Metastases and the Normalization of Tumor Blood Vessels by YCRF-159: A Nero Type of Drug Action", pp. 597–601; European Journal of Cancer, vol. 11, No. 3, 1975, A. Atlierfon "The Effect of (±) 1,2-bis(3,5-dioxopiperazin-1-yl)propane (JCRF-159) on Liver Metastases from a Hamster Lymphoma", 383–388) that the antitumor preparation JCFR-159 (Razzoxane; synthesized by Imperial Cancer Research Fund) (±) 1,2-bis(3,5-dioxopiperazin-1-yl)propane has a certain antimetastic activity, but this preparation is somewhat toxic (LD$_{50}$ 1,000 mg/kg) and side effects (causes leucopenia, thrombocytopenia and dyspeptic phenomena) European Journal of Cancer, vol. 13, No. 8, R. E. Bellet, M. Rozenzweigh, D. D. Van Hoff, J. S. Penta, T. H. Wassermann, F. M. Muggia "JCRF-159: Current Status and Clinical Prospects", pp. 1293–1298.

SUMMARY OF THE INVENTION

The present invention is directed to the provision of such novel compounds which possess antimetastatic activity and low toxicity.

This object is accomplished by novel compounds, 2,6-dimethyl-1,4-dihydropyridine-3,5-dicarboxylic acid esters having the following general formula:

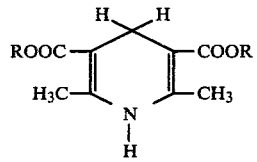

wherein R is a substituted alkyl or terpenyl.

Furthermore, this object is accomplished by a method for preparing 2,6-dimethyl-1,4-dihydropyridine-3,5-dicarboxylic acid esters of the formula:

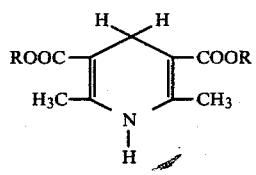

wherein R is a substituted alkyl or terpenyl, wherein according to the present invention, acetoacetic acid esters of the formula CH$_3$COCH$_2$COOR, wherein R is a substituted alkyl or terpenyl, are subjected to reaction with hexamethylenetetramine in the presence of ammonium acetate in the medium of ethanol at the boiling temperature thereof, the esters of acetoacetic acid of the above-mentioned general formula, hexamethylenetetramine and ammonium acetate can be used in the stoichiometric amounts.

The esters of 2,6-dimethyl-1,4-dihydropyridine-3,5-dicarboxylic acid of the formula:

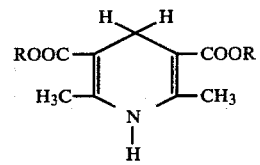

wherein R is a substituted alkyl or terpenyl according to the present invention possessing antimetastatic activity are prepared in good yields under convenient mild conditions from readily available starting compounds.

Furthermore, 2,6-dimethyl-1,4-dihydropyridine-3,5-dicarboxylic acid esters of the above-mentioned formula have a low toxicity (substantially non-harmful)—LD$_{50}$ for this compounds is more than 5,000 mg/kg. Esters of 2,6-dimethyl-1,4-dihydropyridine-3,5-dicarboxylic acid provide no negative effect on normal physiological functions of the live organism.

BEST MODE FOR CARRYING OUT THE INVENTION

The study of physico-chemical properties of the novel compounds according to the present invention has given the following results.

According to the data of elemental analysis, on the one hand, and spectroscopic characteristics, on the other hand, the compounds prepared according to the present invention are actually esters of 2,6-dimethyl-1,4-dihydropyridine-3,5-dicarboxylic acid of the formula:

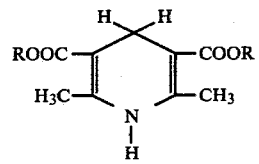

wherein R is a substituted alkyl or terpenyl.

All the above-mentioned novel compounds according to the present invention comprise fine-crystal yellow-green odourless compounds.

Every individual compound has its own molecular and structural formula, melting point and solubility, as well as spectral data.

Thus, disodium salt of carboxylate-methyl ester of 2,6-dimethyl-1,4-dihydropyridine-3,5-dicarboxylic acid having the following structural formula:

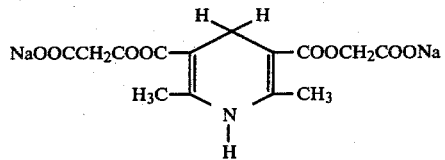

has a melting (decomposition) temperature above 250° C.; it is highly soluble in water, sparingly soluble in alcohol; UV-spectrum in water has maximum of absorption at 236 nm (1 gε=4,20) and 384 nm (1 gε=3.88); IR-spectrum in nujol has the absorption band corresponding to oscillations of the NH-group at 3,375 cm⁻¹.

Menthyl ester of 2,6-dimethyl-1,4-dihydropyridine-3,5-dicarboxylic acid having the following structural formula:

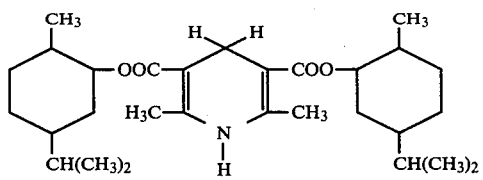

has the melting temperature of 171°–173° C., highly-soluble in alcohol, chloroform, acetone, benzene; insoluble in water; UV-spectrum in alcohol has maximum of absorption at 232 nm (1 gε=4.25) and 372 nm (1 gε=3.91); IR-spectrum in nujol has the absorption bands corresponding to oscillations of NH— group at 3,300 cm⁻¹ and accordingly for C=O at 1,705 cm⁻¹.

The remaining esters of 2,6-dimethyl-1,4-dihydropyridine-3,5-dicarboxylic acid have similar physico-chemical properties.

All the thus-prepared esters of 2,6-dimethyl-1,4-dihydropyridine-3,5-dicarboxylic acid fluoresce with blue-green colour in UV-light.

The common chemical property of the synthesized esters 2,6-dimethyl-1,4-dihydropyridine-3,5-dicarboxylic acid resides in splitting of hydrogen under the effect of oxidizing agents (both inorganic and organic) with conversion to a pyridine derivative according to the scheme:

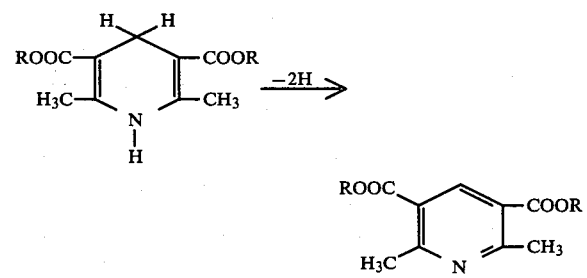

This conversion is accompanied by disappearance, in UV-spectrum characteristic for 2,6-dimethyl-1,4-dihydropyridine-3,5-dicarboxylic acid, of the absorption maximum at 370–380 nm.

The common process for the preparation of esters of 2,6-dimethyl-1,4-dihydropyridine-3,5-dicarboxylic acid comprises condensation of two molecules of acetoacetic acid ester of the formula: $CH_3COCH_2COOR$, wherein R is a substituted alkyl or terpenyl, with hexamethylenetetramine serving as a reagent liberating formaldehyde and ammonia in the presence of ammonium acetate serving as a catalyst and a reagent supplying ammonia. The reaction is carried out in the presence of ethanol at the boiling temperature thereof. All the above-mentioned components can be used in the reaction in the stoichiometric proportions. The reaction occurs according to the following general scheme:

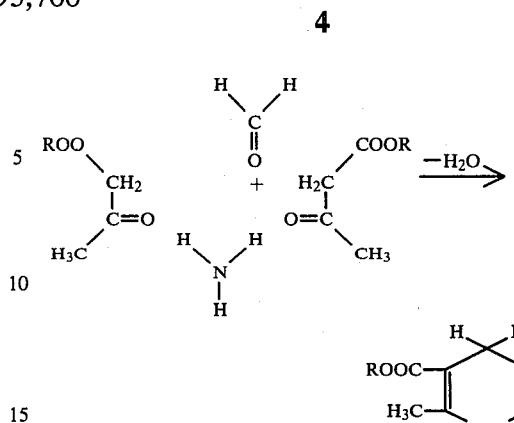

The starting esters of acetoacetic acid of the formula $CH_3COCH_2COOR$, wherein R is a substituted alkyl or terpenyl, are prepared either by re-esterification of ethyl ether of acetoacetic acid upon boiling with a corresponding high-boiling alcohol, or by interaction of a diketene with a corresponding alcohol. Ethers of acetoacetic acid may not be recovered, but, instead, it is possible to prepare esters of 2,6-dimethyl-1,4-dihydropyridine-3,5-dicarboxylic acid stepwise from a diketene, a corresponding alcohol, hexamethylenetetramine and ammonium acetate.

Antimetastatic properties of esters of 2,6-dimethyl-1,4-dihydropyridine-3,5-dicarboxylic acid have been tested on Walker carcinosarcoma, sarcoma 536 and Lewis pneumocarbinoma using mice and rats as test animals. The preparations were administered for 10 days. Two procedures of the administration of these compounds prior to the removal of the primary tumor and introduction of the compound after the removal of the primary tumor. The efficiency of antimetastatic activity of esters of 2,6-dimethyl-1,4-dihydropyridine-3,5-dicarboxylic acid is assessed by the increase of the life duration of the test animals expressed as percentage of the life duration of the animals administered no preparation and serving as the control.

The results thus obtained have shown that the esters of 2,6-dimethyl-1,4-dihydropyridine-3,5-dicarboxylic acid have a pronounced antimetastatic activity.

Thus, disodium salt of carboxylatomethyl ester of 2,6-dimethyl-1,4-dihydropyridine-3,5-dicarboxylic acid administered in doses of 50 and 100 mg/kg during the period after the removal of Walker carcinoma increases the life time of the rest rats by 120 and 93% respectively. The administration of these compounds prior to the removal of the primary tumor also reveals the antimetastatic activity of esters of 2,6-dimethyl-1,4-dihydropyridine-3,5-dicarboxylic acid, though slightly lower. The effect of the compounds is most pronounced in tests with Walker carbinosarcoma on rats; a high efficiency is also noticed for sarcoma 536 with rats; less pronounced is the effect on Lewis lungs carcinoma with mice. The use of esters of 2,6-dimethyl-1,4-dihydropyridine-3,5-dicarboxylic acid provides no negative effect on physiological functions and behaviour of the test animals.

For a better understanding of the present invention, the data on antimetastatic efficiency of certain esters of 2,6-dimethyl-1,4-dihydropyridine-3,5-dicarboxylic acid are summarized and given in the Table hereinbelow.

For a better understanding of the present invention, some specific Examples are given hereinbelow by way of illustration.

EXAMPLE 1

37 g of ethoxycarbonylmethyl ester of 2,6-dimethyl-1,4-dihydropyridine-3,5-dicarboxylic acid are dissolved in 300 ml of hot ethanol and a solution of 9 g of sodium hydroxide in 25 ml of water is added thereto. The resulting yellow slurry is heated for 15 minutes at the temperature of 90° C., added with 100 ml of water and the resulting hot solution is filtered. After cooling, 32 g of disodium carboxylatomethyl or the disodium salt of carboxymethyl ester of 2,6-dimethyl-1,4-dihydropyridine-3,5-dicarboxylic acid (69% of the theoretical yield) in the form of a yellow crystalline compound having its melting point above 250° C. The compound is recrystallized from a 70% ethanol.

Found, %: C 33.4; H 5.3; N 3.0%; $C_{13}H_{13}NO_8Na_2.6H_2O$. Calculated, %: C 33.5; H 5.4; N 3.0%.

EXAMPLE 2

A mixture of 31 g of beta-cyanoethyl ester of acetoacetic acid, 12.3 g of hexamethylenetetramine, 14 g of ammonium acetate and 200 ml of ethanol are refluxed for 30 minutes. After cooling, there are recovered 28 g (92% of the theoretical value) of beta-cyanoethyl ester of 2,6-dimethyl-1,4-dihydropyridine-3,5-dicarboxylic acid as a yellow crystalline substance having, after recrystallization from ethanol, melting point of 165°–169° C.

Found: C 58.7; H 5.6; N 14.2%; $C_{15}H_{17}NO_4$. Calculated: C 59.9; H 5.7; N 13.9%.

EXAMPLE 3

In 400 ml of benzene there are dissolved 100 g of menthol, added with 1 ml triethylamine, at refluxing and stirring for one hour there are added 55 ml of diketene and benzene is distilled-off under a reduced pressure (150 mm Hg). The remaining oily product consisting mainly of methyl ether of acetoacetic acid is dissolved in 400 ml of ethanol, added with 28 g of hexamethylenetetramine and 5 g of ammonium acetate and the reaction mixture is boiled on a water bath for 30 minutes. After cooling, the precipitated yellow substance is filtered-off and recrystallized from ethanol. There are obtained 105 g (69% of the theoretical value) of menthyl ester of 2,6-dimethyl-1,4-dihydropyridine-3,5-dicarboxylic acid in the form of a bright-yellow crystalline substance having its melting temperature of from 180°–182° C.

Found, %: C 73.7; H 9.9; N 2.8. $C_{29}H_{47}NO_4$. Calculated; %: C 73.6; H 10.0; N 3.0.

EXAMPLE 4

A mixture of 22.2 g of bornyl ester of acetoacetic acid 7 g of hexamethylenetetramine, 3.9 g of ammonium acetate and 150 ml of ethyl alcohol is refluxed for 30 minutes. After cooling a yellow substance is precipitated which is then filtered-off and recrystallized from ethanol. There are obtained 12 g (52% of the theoretical value) of bornyl ester of 2,6-dimethyl-1,4-dihydropyridine-3,5-dicarboxylic acid as a yellow crystalline substance having melting point of 171°–173° C.

Found, %: C 74.1; H 10.9; N 2.9. $C_{29}H_{43}NO_4$ Calculated, %: C 74.2; H 10.8; N 3.0.

INDUSTRIAL APPLICABILITY

The novel compounds, i.e. esters of 2,6-dimethyl-1,4-dihydropyridine-3,5-dicarboxylic acid according to the present invention having the following general formula:

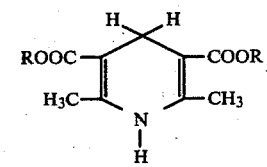

wherein R is a substituted alkyl or terpenyl, can be useful as substances possessing antimetastatic properties in the chemotherapy of tumors.

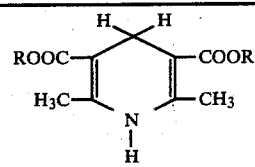

Effect of esters of 2,6-dimethyl-1,4-dihydropyridine-3,5-dicarboxylic acid on life time of test animals

| Compound of the formula | Mode of administration of the compound | Daily dose of the compound, mg/kg | Life duration, % of the control | | |
|---|---|---|---|---|---|
| | | | Sarcoma 536 (rats) | Walker carcinosarcoma (rats) | Lewis lungs carcinoma (mice) |
| wherein R is $CH_2COONa$ (disodium carboxylatemethyl ester) | Before the removal of the primary tumor | 50 | — | 130 | — |
| | | 100 | 152 | 150 | — |
| | | 150 | 138 | — | — |
| | After the removal of the primary tumor | 50 | 129 | 220 | — |
| | | 100 | — | 193 | 120 |
| | | 150 | 132 | 112 | 113 |
| wherein R is $C_{10}H_{19}$ (menthyl ester) | Prior to the removal of the primary tumor | 150 | — | 116 | — |
| | | 300 | — | 165 | — |

We claim:
1. 2,6-dimethyl-1,4-dihydropyridine-3,5-dicarboxylic acid esters of the general formula:

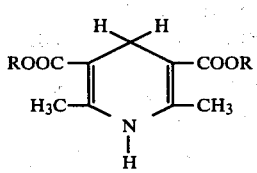
wherein R is cycloterpenyl, or branched or linear $C_1$–$C_5$ alkyl substituted by COOX wherein X is hydrogen or a salt forming cation, or methyl substituted by phenyl or carboxylate.
2. 2,6-dimethyl-1,4-dihydropyridine-3,5-dicarboxylic acid esters of the general formula:
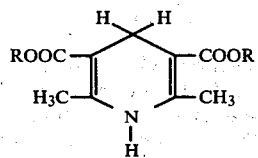
wherein R is carboxylatomethyl, sodiumcarboxylatomethyl, cyanoethyl, menthyl or bornyl.
* * * * *